United States Patent [19]

Cohen

[11] 4,224,945
[45] Sep. 30, 1980

[54] INFLATABLE EXPANSIBLE SURGICAL PRESSURE DRESSING

[76] Inventor: Jonathan Cohen, 96 Larchwood Dr., Cambridge, Mass. 02138

[21] Appl. No.: 938,025

[22] Filed: Aug. 30, 1978

[51] Int. Cl.³ ............................................ A61B 17/12
[52] U.S. Cl. .................................... 128/325; 128/155; 128/300
[58] Field of Search ........ 128/325, 326, 327, 155–158, 128/163

[56] References Cited

U.S. PATENT DOCUMENTS

| | | | |
|---|---|---|---|
| 718,408 | 1/1903 | Wetmore | 128/118 |
| 817,288 | 4/1906 | Whedon | 128/268 |
| 2,614,565 | 10/1952 | Packer | 128/327 |
| 2,839,062 | 1/1958 | Jordan | 128/327 |
| 3,089,488 | 5/1963 | Owens | 128/156 |
| 3,171,410 | 3/1965 | Towle et al. | 128/155 |
| 3,952,735 | 4/1976 | Wirtschaffer et al. | 128/163 |
| 4,005,709 | 2/1977 | Lacrdal | 128/155 |
| 4,026,290 | 5/1977 | Brooker et al. | 128/260 |

FOREIGN PATENT DOCUMENTS 25652 of 1910 United Kingdom ..................... 128/163

Primary Examiner—William E. Kamm

[57] ABSTRACT

A dressing for application to a skin surface promotes healing of lesions by the simultaneous selective localized application of compression and tension. The dressing comprises an elastically expansible pressure pouch, secured to the central part of the lower surface of an inelastic sheet, the sheet extending laterally beyond the pouch in every direction. A continuous adhesive zone completely surrounds the pouch for adhering the dressing to the intact skin surface surrounding the lesion. Means are provided to increase the pressure within the pouch after the dressing adhesive zone has been secured to the intact skin surface, whereby expansion of the pouch moves the central part of the sheet away from the lesion and maintains it there, thereby exerting tension on the sheet margin. The tension is everywhere centripetally directed and is transmitted through the adhesive zone to the intact skin surrounding the lesion. Pressure of the expanded pouch between the inelastic sheet and the lesion exerts compression on the lesion.

8 Claims, 8 Drawing Figures

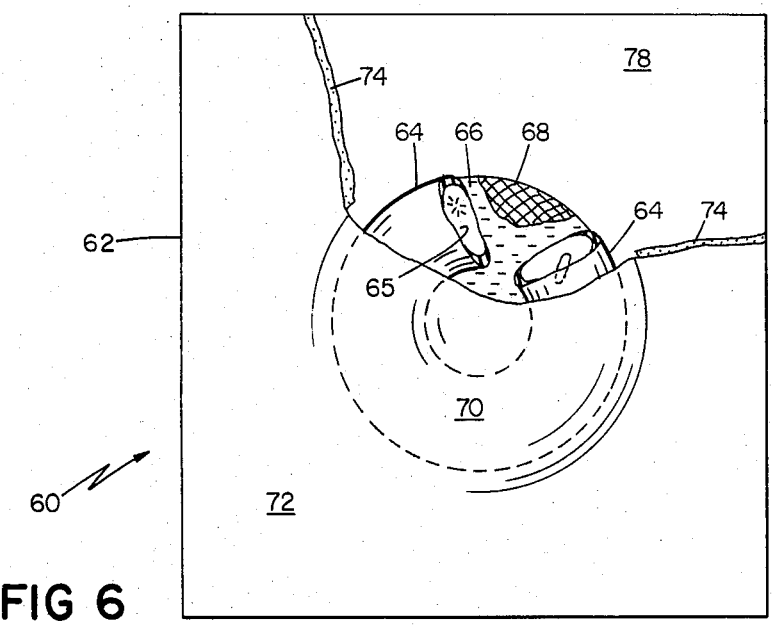
FIG 6
FIG 7
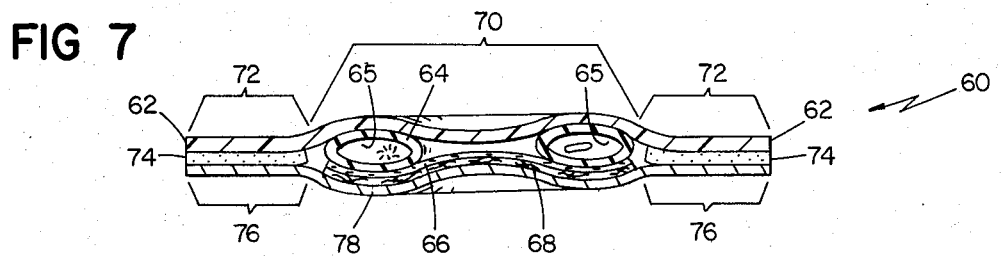
FIG 8
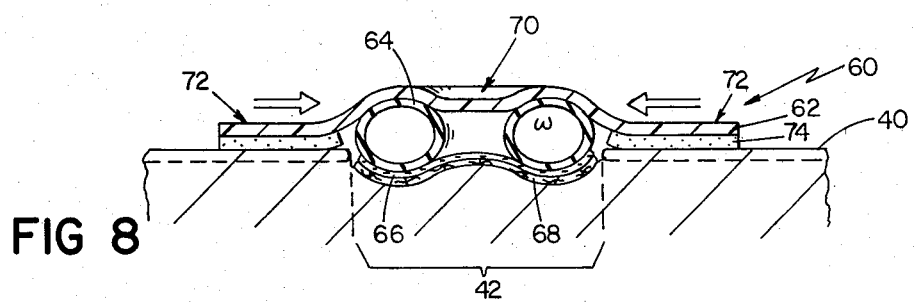

INFLATABLE EXPANSIBLE SURGICAL PRESSURE DRESSING

This invention relates to a dressing applicable to decubitus, varicose and other ulcers that are slow to heal, and to other similar lesions.

Prior art dressings for lesions and wounds have in general been designed for the purpose of applying pressure to wounds for hemostasis (to stop bleeding), as shown, for example, in U.S. Pat. No. 3,171,410 to Towle, Jr. et al., or for the protection of wounds from mechanical injury without the application of pressure. Such dressings have in some cases been designed to provide means to apply medicaments, or means to absorb secretions from the wound. However, prior art dressings have not been designed to apply two particular medical principles to the specific case of slow-healing lesions such as ulcers.

First, in the healing of wounds generally, it is known to be desirable to exert tension on the intact skin surrounding the lesion in order to promote healing. In the healing of wounds that are not slow to heal, such as incisions, this tension is supplied physiologically by the contraction of the fibrous elements in the exudate of the wound, and in the repair tissue below the skin. However, in chornic ulcers, the fibrous tissue forms a scar that matures at the margin of the ulcer but does not continue to orient the fibrous tissue in the healing direction. Therefore, it is an object of this invention to provide means to exert such tension on the intact skin surrounding the ulcer in order to promote healing of chronic ulcers, or ulcers which may be becoming chronic.

Secondly, in the healing of ulcers in particular, healing proceeds from the margins inwardly, and it is a frequently encountered difficulty that the edge of the growing skin tends to "heap up" at the margin of the ulcer. This occurs both because of inadequate tension on the intact skin surrounding the ulcer, and because the exudate that collects in the ulcer forms an obstacle to the inward growth of the new skin. It is therefore another object of the invention to provide means to exert a compressive force on the surface of the ulcer, which tends to promote inward growth of the new skin and to overcome the tendency of the new growth to build up at the ulcer margin.

It is a further object of this invention to provide a dressing that is especially suited to application to slow-healing lesions such as ulcers, and that promotes the healing of such lesions by the selective application of compression and tension in combination.

It is also an object of this invention to provide a dressing that is applicable to other types of lesions, such as operative incisions in which the skin edges were approximated only with difficulty.

Additionally, it is an object of this invention to provide a dressing that is useful in the reduction of swelling near joints having irregular bony contours, such as the ankle or knee, where the bone structure prevents an annular elastic bandage from being effective.

Accordingly, the present invention provides a dressing for application to a skin surface for promoting healing of wounds such as ulcers by the simultaneous selective localized application of compression and tension. The dressing comprises an elastically expansible pouch adapted to be pressurized and of a size corresponding with that of a lesion to be dressed. The dressing further comprises an inelastic sheet having the pouch secured to its lower surface substantially centrally of the sheet so as to define a sheet pressure region. The sheet extends laterally beyond the pouch in every direction to define a continuous peripheral sheet tension zone.

An adhesive layer is provided on the continuous peripheral sheet tension zone lower surface, to produce an adhesive zone completely surrounding the pouch for adhering the dressing to the intact skin surface region surrounding the lesion and positioning the pouch adjacent the lesion. The dressing further includes pouch-inflating means for increasing the pressure within the pouch to a desired value or extent after the adhesive zone has been secured to the intact skin surface.

The expansion of the pouch to the desired extent after the dressing has been adhered to the skin moves the sheet member pressure region away from the lesion and maintains the pressure region in such position, thereby exerting tension on the continuous peripheral sheet tension zone, the tension being everywhere centripetally directed and being transmitted through the adhesive region to the intact skin surrounding the lesion, and at the same time, the pressure of the pouch against the inelastic sheet pressure region and against the lesion exerts compression on the lesion.

In a first preferred embodiment, the sealed pressure pouch is generally lens-shaped in form so that after expansion of the pouch to the desired extent it exerts compression generally over the entire surface of the lesion. The pouch has upper and lower walls or faces, the upper wall being secured to the lower surface of the sheet, and the pouch includes on its lower wall or face a layer of abosrptive material together with a water soluble film carrying a medically active substance, the latter being disposed between the pouch wall and the layer of absorptive material.

In a second preferred embodiment, the sealed pressure pouch is toroidal in form, so that after expansion of the pouch to the desired value or extent the expansion of the pouch against the inelastic sheet pressure region and against the lesion exerts compression selectively on the marginal area of the lesion adjacent the intact skin. Absorptive and medicated layers may be provided as in the first preferred embodiment.

Other objects, features and advantages will appear from the following description of a preferred embodiment of the invention, taken together with the drawing, in which:

FIG. 6 is a plan view partly broken away of the dressing of another embodiment of the invention;

FIG. 7 is a section taken on line 7—7 of FIG. 6; and

FIG. 8 is a view in section of the dressing of FIGS. 6 and 7 in inflated condition.

Figure 1:
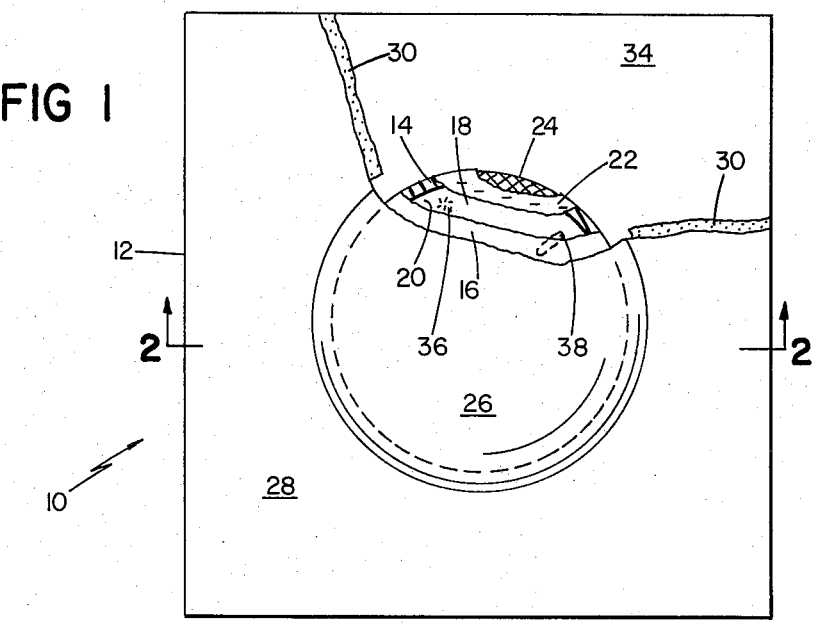
FIG. 1 is a plan view, partially broken away, of the dressing of the invention.

Referring now to the drawing, and particularly to FIG. 1, the dressing 10 of the invention comprises an inelastic sheet 12, of rectangular shape in this embodiment, although it may be of any convenient shape depending on the lesion to which it is to be applied.

Figure 2:
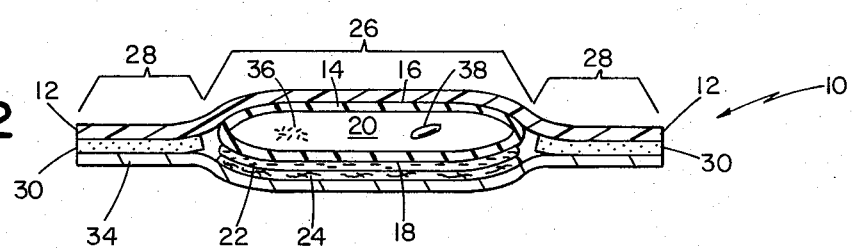
FIG. 2 is a section taken on the line 2—2 of FIG. 1.

Referring particularly to FIG. 2, the dressing 10 is seen in section, taken on line 2—2 of FIG. 1. An elastically deformable sealed pressure pouch 14 is generally lens-shaped, having upper and lower walls 16 and 18 enclosing an internal region 20. The size of the pressure pouch is determined by the size of the lesion to be dressed; the pouch should have a diameter that is about one-half inch than the diameter of the lesion.

A layer 22 of water soluble film containing any appropriate drug or medicament (such as antibiotic, steroid, antiseptic, enzyme) is provided on lower pouch wall 18, below which is a further layer 24 of gauze for the absorption of exudate from the lesion. This gauze may be impregnated if desired with granules of a dessicant to provide absorption of fluid by the dressing.

The medicated film layer 22 and gauze layer 24 are not essential to the practice of the invention and may be omitted in circumstances where the selective application of compression and tension is alone desired.

Pressure pouch 14 is secured to the lower surface of sheet 12 substantially centrally of the sheet and defining a sheet pressure region 26. The sheet extends laterally beyond the pouch in every direction to define a continuous peripheral sheet tension zone 28 surrounding the sheet pressure region 26. The continuous peripheral sheet tension zone 28 is indicated in two portions in the sectional view of FIG. 2.

An adhesive layer 30 is provided on the lower surface (proximal to the skin surface) of sheet 12 in the continuous peripheral sheet tension zone 28, defining a continuous adhesive zone 32 completely surrounding pouch 14 for adhering the dressing 10 to the intact skin surface region surrounding the ulcer and positioning lower wall 18 of pouch 14 proximal to the ulcer.

A readily removable temporary protective release sheet 34 is provided for dressing 10, to cover dressing adhesive zone 32 and gauze layer 24.

Pouch inflating means are provided for increasing the pressure within pouch 14. While this might take the form of a tube to which a pump could be connected, in the preferred embodiment it comprises a powder 36 and a liquid disposed within the pouch, the liquid being supplied in a sealed frangible capsule 38. The powder and liquid are such that when mixed they will combine to evolve a gas. An example of such a combination is sodium carbonate and acetic acid, but any gas-producing combination can be used. The capsule is broken manually within the pouch by pinching the dressing. The quantities of powder and liquid must be selected with the object of generating the necessary quantity of gas to exert the desired pressure on the lesion and tension on the surrounding intact skin. Alternatively other devices for the generation of gas within the pouch could be used, for example, an inflation tube connectible to a pump or to a pressurized capsule.

Figure 5:
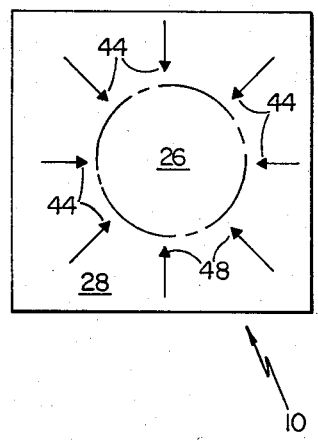
FIG. 5 shows the direction of the tension selectively applied by the dressing of the invention.
Figure 3:
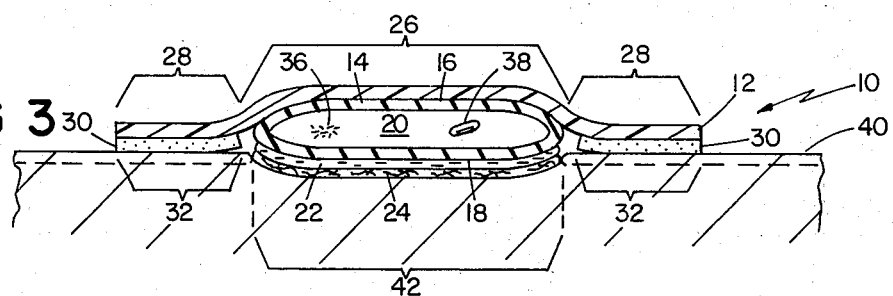
FIG. 3 is the same view as in FIG. 2 but shows the dressing in place on a skin surface.
Figure 4:
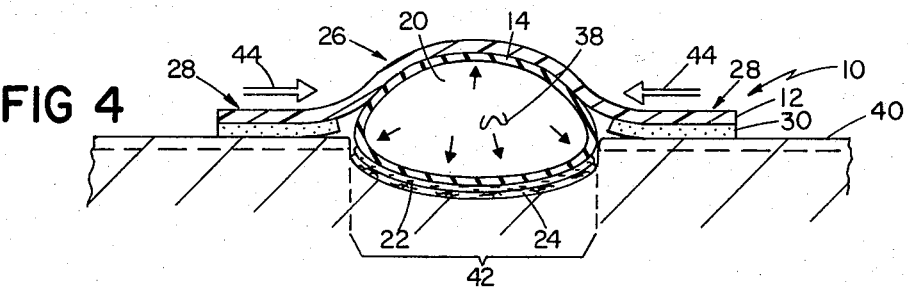
FIG. 4 is similar to FIG. 3 but shows the sealed pressure pouch in inflated condition.

The application of the dressing and the operation of the invention will now be described, referring now particularly to FIGS. 3 and 4 which show the dressing 10 of the invention applied to the skin 40 of a patient. Referring to FIG. 3, release sheet 34 has been removed, and dressing adhesive zone 32 has been adhered to the intact skin surrounding the region 42 of the ulcer or other lesion before pouch 14 has been inflated. As shown in FIG. 4, capsule 38 has then been broken and the powder and liquid have evolved a gas within pouch 14, expanding the latter and moving sheet pressure region 26 away from the ulcer. This change in configuration of region 26 of the inelastic sheet exerts tension on continuous peripheral sheet tension zone 28, and this tension is everywhere centripetally directed, as seen more particularly in FIG. 5 and indicated therein and in FIG. 4 by arrows 44. The tension is transmitted through adhesive region 32 to the intact skin surrounding the ulcer, tending to draw the skin edges inwardly toward the inner portion of the ulcer. Since the pressure pouch is sealed, it will be appreciated that the pouch does not deflate, but maintains the sheet pressure region in the changed position so that tension is thereafter maintained on the intact skin.

At the same time the expansion of pouch 14 causes pressure against sheet pressure region 26 and against the region of the ulcer. Compression is therefore selectively exerted over the surface of the ulcer.

Referring now to FIGS. 6, 7 and 8, an alternative embodiment of the dressing of the invention is shown. This embodiment is one having particular utility in the treatment of ulcers; in this embodiment, the expansion pouch is toroidal or doughnut-shaped, to provide compression particularly at the edges of the ulcer. Dressing 60 comprises an inelastic but flexible sheet 62, which may be rectangular or circular or of any other desired shape. An elastically deformable sealed pressure pouch 64 in the form of a ring, or torus, which is substantially flattened in the unexpanded state shown in FIG. 6, is secured to the lower surface of sheet 62. The pouch encloses a single ring-shaped internal region 65. The size of the pressure pouch is determined by the size of the ulcer to be dressed; the tubular pouch should cover the outer margin of the ulcer.

A layer 66 of water soluble film containing any appropriate drug or medicament (such as an antibiotic, steroid, antiseptic or enzyme) is provided on the lower portion of pouch 64. Below film layer 66, a further layer 68 of gauze is provided, for the absorption of exudate from the lesion. This gauze may be impregnated if desired with granules of a dessicant to provide absorption of fluid by the dressing.

Pressure pouch 64 is secured to the lower surface of sheet 62 through an annular region located substantially centrally of the sheet. Since the sheet is inelastic, the central portion of sheet 62 will be carried outwardly along with the portions attached to pouch 64 when pouch 64 is expanded. Therefore the annular region through which pouch 64 is attached to sheet 62 defines an annular sheet pressure region 70 surrounding the central substantially pressure-free zone. The sheet extends laterally beyond the pouch in every direction to define a continuous peripheral sheet tension zone 72 surrounding the sheet pressure region 70.

An adhesive layer 74 is provided on the lower surface (proximal to the skin surface) of continuous peripheral sheet tension zone 72, defining a continuous adhesive zone 76 completely surrounding pouch 64 for adhering the dressing 60 to the intact skin surface region surrounding the ulcer and positioning the lower wall of pouch 64 proximal to the outer margin of the ulcer.

A readily removable, temporary protective sheet 78 is provided for dressing 60, to cover adhesive zone 76 and gauze layer 68.

Pouch-inflating means are provided and may be of the types described for the embodiment of FIGS. 1-5.

Referring now to FIG. 8, dressing 60 is shown after application to the skin of a patient and subsequent inflation of pouch 64. Protective sheet 78 has been removed, and adhesive zone 76 has been adhered to the intact skin surrounding the region 80 of the ulcer and sheet pressure region 70 is moved away from the ulcer. This motion of region 70 of the inelastic sheet exerts tension on continuous peripheral sheet tension zone 72, and this tension is everywhere centripetally directed, as shown for the embodiment of FIGS. 1-5. The tension is transmitted through adhesive region 74 to the intact skin surrounding the ulcer, tending to draw the skin edges inwardly toward the inner portion of the ulcer.

At the same time the expansion of the closed tubular pouch 64 causes pressure against sheet member pressue region 70 and against the marginal portion of the ulcer. As seen in FIG. 8, compression is selectively exerted over the marginal portion of the ulcer. As has been explained, such compression acts to overcome the tendency of the new skin to "heap up" at the margin of the ulcer, and encourages the skin to grow inwardly over the ulcer surface. Meanwhile the central, unhealed portion of the ulcer is forced gently upwardly against gauze layer 68 and medicated layer 66, for absorption of exudate from the ulcer.

The expansible pouch may in alternative embodiments be of a configuration other than a torus, such as for example a hollow square or rectangle or oval, as appropriate to the shape of the area to be treated, and intended to cover only a marginal portion of the lesion to be dressed.

What is claimed is:

1. A dressing for application to a skin surface for promoting healing of lesions by the simultaneous selective localized application of compression and tension, comprising
   an elastically expansible closed pressure pouch of a size corresponding to that of a lesion to be dressed,
   a sheet inelastic relative to said pressure pouch and having an upper and a lower surface, said pouch being secured to said sheet lower surface substantially centrally of said sheet and defining a sheet pressure region,
   said sheet extending laterally beyond said pouch in every direction to define a continuous peripheral sheet tension zone,
   an adhesive layer on said continuous peripheral sheet tension zone lower surface defining a continuous adhesive zone completely surrounding said pouch for adhering said dressing to the intact skin surface surrounding said lesion and positioning said pouch adjacent said lesion, and
   pouch-inflating means for increasing the pressure within said pouch after said dressing adhesive zone has been secured to said intact skin surface,
   whereby expansion of said pouch moves said sheet pressure region away from said lesion and maintains said region in such position, thereby exerting tension on said continuous peripheral sheet tension zone, said tension being everywhere centripetally directed and being transmitted through said adhesive region to the intact skin surrounding said lesion, and
   whereby pressure of said expanded pouch against said inelastic sheet pressure region and against said lesion exerts compression on said lesion.

2. The dressing of claim 1, wherein said pressure pouch is toroidal in form,
   whereby after expansion of said pouch to said desired value, the pressure of said pouch against said inelastic sheet pressure region and against said lesion exerts compression selectively on the marginal area of said lesion adjacent said intact skin.

3. The dressing of claim 1, wherein said pressure pouch is generally lens-shaped in form,
   whereby after expansion of said pouch to said desired value, the pressure of said pouch against said inelastic sheet pressure region and against said lesion exerts compression generally over the entire surface of the lesion.

4. The dressing of claim 1, said expansible pouch having upper and lower walls,
   said pouch upper wall being secured to said sheet lower surface, and said pouch providing on said lower wall a layer of absorptive material.

5. The dressing of claim 1, said expansible pouch having upper and lower walls,
   said pouch upper wall portion being secured to said sheet lower surface, and said pouch providing on said lower wall portion a layer of water soluble film carrying a medically active substance.

6. The dressing of claim 1, said expansible pouch having upper and lower walls,
   said pouch upper wall being secured to said sheet lower surface, and
   said pouch providing on said lower wall portion a first layer of absorptive material, and
   a second layer of water soluble film carrying a medically active substance,
   said first layer being adjacent said pouch, and said second layer being spaced from said pouch by said first layer.

7. A dressing for application to a skin surface for promoting healing of lesions by the simultaneous selective regional application of compression and tension, comprising
   an elastically expansible closed pressure pouch of a size corresponding with that of a lesion to be dressed, said pouch being generally lens-shaped in form, and having upper and lower walls
   a sheet inelastic relative to said pressure pouch and having an upper and a lower surface, said pouch upper wall being secured to said sheet lower surface substantially centrally of said sheet and defining a sheet pressure region,
   said pouch lower wall providing a first layer of absorptive material and a second layer of watersoluble film carrying a medically active substance, said second layer being between said pouch and said first layer,
   said sheet extending laterally beyond said pouch in every direction to define a continuous peripheral sheet tension zone,
   an adhesive layer on said continuous peripheral sheet tension zone lower surface, defining a continuous dressing adhesive zone completely surrounding said pouch for adhering said dressing to the intact skin surface region surrounding said lesion and positioning said pouch adjacent said lesion, and
   pouch-inflating means for increasing the pressure within said pouch after said dressing adhesive zone has been secured to said intact skin surface,
   whereby expansion of said pouch moves said sheet pressure region away from said lesion and maintains said region in such position, thereby exerting tension on said continuous peripheral sheet tension zone, said tension being everywhere centripetally directed and being transmitted through said adhesive region to the intact skin surrounding said lesion, and whereby pressure of said expanded pouch against said inelastic sheet pressure region and against said lesion exerts compression generally over the entire surface of said lesion.

8. A dressing for application to a skin surface for promoting healing of lesions by the simultaneous selective regional application of compression and tension, comprising an elastically expansible closed pressue pouch of a size corresponding with that of a lesion to be dressed, said pouch being generally toroidal in form, and having upper and lower walls a sheet inelastic relative to said pressure pouch and having an upper and a lower surface, said pouch upper wall being secured to said sheet lower surface substantially centrally of said sheet and defining a sheet pressure region.

said pouch lower wall providing a first layer of absorptive material and a second layer of water soluble film carrying a medically active substance, said second layer being between said pouch and said first layer, said sheet extending laterally beyond said pouch in every direction to define a continuous peripheral sheet tension zone, an adhesive layer on said continuous peripheral sheet tension zone lower surface, defining a continuous dressing adhesive zone completely surrounding said pouch for adhering said dressing to the intact skin surface region surrounding said lesion and positioning said pouch proximal to said lesion, and pouch-inflating means for increasing the pressure within said pouch after said dressing adhesive zone has been secured to said intact skin surface, whereby expansion of said pouch moves said sheet pressure region away from said lesion and maintains said region in such position, thereby exerting tension on said continuous peripheral sheet tension zone, said tension being everywhere centripetally directed and being transmitted through said adhesive region to the intact skin surrounding said lesion, and whereby pressure of said expanded pouch against said inelastic sheet pressure region and against said lesion exerts compression selectively on the marginal area of said lesion adjacent said intact skin.

* * * * *

UNITED STATES PATENT AND TRADEMARK OFFICE
CERTIFICATE OF CORRECTION

PATENT NO. : 4,224,945
DATED : September 30, 1980
INVENTOR(S) : Jonathan Cohen

It is certified that error appears in the above-identified patent and that said Letters Patent are hereby corrected as shown below:

Under references cited, "La̲erdal" is misspelled;

Col. 1, line 27, "chronic" is misspelled;

Col. 2, line 33, "absorptive" is misspelled;

Col. 5, line 10, "pressure" is misspelled;

Col. 7, line 10, "pressure" is misspelled.

Signed and Sealed this

Tenth Day of February 1981

[SEAL]

Attest:

RENE D. TEGTMEYER

Attesting Officer

Acting Commissioner of Patents and Trademarks